(12) United States Patent
Croce

(10) Patent No.: US 7,728,189 B2
(45) Date of Patent: Jun. 1, 2010

(54) HUMAN CHRONIC LYMPHOCYTIC LEUKEMIA MODELED IN MOUSE BY TARGETED TCL1 EXPRESSION

(75) Inventor: Carlo M. Croce, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 45 days.

(21) Appl. No.: 12/080,907

(22) Filed: Apr. 7, 2008

(65) Prior Publication Data
US 2008/0256650 A1 Oct. 16, 2008

Related U.S. Application Data

(63) Continuation of application No. 10/427,629, filed on Apr. 29, 2003, now abandoned.

(60) Provisional application No. 60/376,464, filed on Apr. 29, 2002.

(51) Int. Cl.
*A01K 67/027* (2006.01)
(52) U.S. Cl. .......................................... 800/18; 800/13
(58) Field of Classification Search .................. 800/18, 800/13
See application file for complete search history.

(56) References Cited

U.S. PATENT DOCUMENTS

| | | | |
|---|---|---|---|
| 4,736,866 | A | 4/1988 | Leder et al. |
| 4,870,009 | A | 9/1989 | Evans et al. |
| 4,873,191 | A | 10/1989 | Wagner et al. |
| 5,550,316 | A | 8/1996 | Mintz |

FOREIGN PATENT DOCUMENTS

| | | |
|---|---|---|
| WO | WO 88/00239 | 1/1988 |
| WO | WO 90/05188 | 5/1990 |
| WO | WO 92/11757 | 7/1992 |

OTHER PUBLICATIONS

Bichi et al. (2002) PNAS, V. 99(10), 6955-6969.*
Narducci et al. (2000) Cancer Research, V. 60, 2095-2100.*
Virgilio et al. (1998) PNAS, vol. 95, 3885-3889.*
Takizawa et al. (1998) Jpn. J. Cancer Res., vol. 89, 712-718.*
Andreef, M., et al., "Discrimination of Human Leukemia Subtypes by Flow Cytometric Analysis of Cellular DNA and RNA," *Blood*, 55(2): 282-293 (1980).
ar-Rushdi, A., et al., "Differential Expression of the Translocated and the Untranslocated *c-myc* Oncogene in Burkett Lymphoma," *Science*, 222: 390-393 (1983).
Bichi, R., et al., "Human Chronic Lymphocytic Leukemia Modeled in Mouse by Targeted *TCL1* Expression," *Proc. Natl. Acad. Sci. USA*, 99(10): 6955-6960 (2002).
Boumsell, L., et al., "Some Chronic Lymphocytic Leukemia Cells Bearing Surface Immunoglobulins Share Determinants with T Cells," *Eur. J. Immunol.*, 8: 900-904 (1978).
Brinster, R.L., et al., "Somatic Expression of Herpes Thymidine Kinase in Mice Following Injection of a Fusion Gene Into Eggs," *Cell*, 27: 223-231 (1981).
Caligaris-Cappio, F., et al., "Infrequent Normal B Lymphocytes Express Features of B-Chronic Lymphocytic Leukemia," *J. Exp. Med.*, 155: 623-628 (1982).
Campbell, K.H.S., and Wilmut, I., "Totipotency or Multipotentiality of Cultured Cells: Applications and Progress," *Theriogenology* 47:63-72 (1997).
Chen, X., et al., "Evidence for Selection of a Population of Multi-Reactive B Cells into the Splenic Marginal Zone," *Int. Immunol.*, 9(1): 27-41 (1982).
Costantini, F., et al., "Introduction of the Rabbit β-globin gene into the Mouse Germ Line," *Nature*, 294: 27-41 (1997).
Croce, C.M., "Role of Chromosome Translocations in Human Neoplasia," *Cell*, 49: 155-156 (1987).
Dalla-Favera, R., et al., "Human c-myc onc Gene is located on the Region of Chromosome 8 that is Translocated in Burkitt Lymphoma Cells," *Proc. Natl. Acad. Sci. USA*, 79: 7824-7827 (1982).
Hammer, R.E., et al., "Production of Transgenic Rabbits, Sheep and Pigs by Microinjection," *Nature*, 315: 680-683 (1985).
Hammer, R.E., et al., "Genetic Engineering of Mammalian Embryos," *J. Animal Sci.*, 63: 269-278 (1986).
Harbers, K., et al., "Microinjection of Cloned Retroviral Genomes into Mouse Zygotes: Integration and Expression in the Animal," *Nature*, 293: 540-542 (1981).
Hardy, R.R., et al., "Distinctive Developmental Origins and Specificities of Murine CD5+ B Cells," *Immunol. Rev.*, 137: 91-118 (1994).
Hardy, R.R., et al., "Resolution and Characterization of Pro-B and Pre-pro-B Cell Stages in Normal Mouse Bone Marrow," *J. Exp. Med.*, 173: 1213-1225 (1991).
Hardy, R.R., et al., "Purification and Coupling of Fluorescent Proteins for Use in Flow Cytometry," in The Handbook of Experimental Immunology, 4th Ed., Weir, D.M., et al. (Eds.), Blackwell Scientific Pub. Ltd., Edinburgh, Chapter 31, 31.1-31.12 (1986).
Hayakawa, K., et al., "Normal, Autoimmune, and Malignant CD5+ B Cells: The LY-1 B Lineage?," *Annu. Rev. Immunol.* 6: 197-218 (1988).
Hogan, et al., Manipulating the Mouse Embryo: A Laboratory Manual, Cold Spring Harbor Laboratory (1986).
Hoyer, K.K., et al., "TCL1 Oncogene-Induced B-Cell Neoplasia: A Role for Antigen Receptor Activation," Proceedings of the American Association for Cancer Research Annual Meeting, vol. 43, Mar. 2002, p. 281, XP001536628 & 93rd Annual Meeting of the American Association for Cancer Research; San Francisco, California, USA; Apr. 6-10, 2002 ISSN: 0197-016X (Abstract No. XP-001536628).
Hoyer, K.K., et al., "Dysregulated TCL1 Promotes Multiple Classes of Mature B Cell Lymphoma," *Proc. Natl. Acad. Sci. USA*, 99(22): 14392-14397 (2002).
http://www.ncbi.nlm.nih.gov/BLAST.

(Continued)

*Primary Examiner*—Anne Marie S Wehbe
(74) *Attorney, Agent, or Firm*—Hamilton, Brook, Smith & Reynolds, P.C.

(57) ABSTRACT

Transgenic animals containing a nucleic acid sequence encoding TCL1 operably linked to transcriptional control sequences directing expression to B cells are described. Such transgenic animals provide a useful animal model system for human B cell chronic lymphocytic leukemia.

7 Claims, 9 Drawing Sheets

OTHER PUBLICATIONS

Jaenisch, R., "Transgenic Animals," *Science*, 240: 1468-1474 (1988).
Kantor, A.B., et al., "Origin of Murine B Cell Lineages," *Annu. Rev. Immunol.*, 11: 501-538 (1993).
Kantor, A.B., et al., "An Unbiased Analysis of VH-D-JH Sequences from B-1a, B-1b, and Conventional B Cells," *J. Immunol.*, 158: 1175-1186 (1997).
Kantor, A.B., "The Development and Repertoire of B-1 Cells (CD5 B Cells)," *Immunol. Today*, 12(11): 389-391 (1991).
Landis, S.H., et al., "Cancer Statistics," *CA Cancer J. Clin.*, 48: 6-29 (1998).
Lanier, L.L., et al., "Expression of Lyt-1 Antigen on Certain Murine B Cell Lymphomas," *J. Exp. Med.*, 153: 998-1003 (1981).
Li, Y.-S., et al., "Identification of the Earliest B Lineage Stage in Mouse Bone Marrow," *Immunity*, 5: 527-535 (1996).
Li, Y.-S., et al., "The Regulated Expression of B Lineage Associated Genes During B Cell Differentiation in Bone Marrow and Fetal Liver," *J. Exp. Med.*, 178: 951-960 (1993).
Mullins, L.J. and Mullins, J.J., "Transgenesis in the Rat and Larger Mammals," *J. Clin. Invest.*, 98(11): S37-S40 (1996).
Narducci, M.G., et al., "TCL1 is Overexpressed in Patients Affected by Adult T-Cell Leukemias," *Cancer Res.*, 57: 5452-5456 (1997).
Narducci, M.G., et al., "Regulation of TCL1 Expression in B- and T-Cell Lymphomas and Reactive Lymphoid Tissues," *Cancer Res.*, 60: 2095-2100 (2000).
Nilsson, K., "The Control of Growth and Differentiation in Chronic Lymphocytic Leukemia (B-CLL) Cells," in Chronic Lymphocytic Leukemia: Scientific Advances & Clinical Development, Cheson, B.D (Ed.), 33-61 (1992).
Palmiter, R.D., et al., "Germ-line Transformation of Mice," *Ann. Rev. Genet.*, 20: 465-499 (1986).
Pennell, C.A., et al., "Restricted Ig Variable Region Gene Expression Among Ly-1+ B Cell Lymphomas," *J. Immunol.*, 141: 2788-2796 (1988).
Phillips, J.A., et al., "The NZB Mouse as a Model for Chronic Lymphocytic Leukemia," *Cancer Res.*, 52: 437-443 (1992).
Rai, K., et al., "Chronic Lymphocytic Leukemia," in Hematology: Basic Principles and Practice, Hoffman, et al., (Eds.), Churchill Livingstone, NY, Chapter 83, 1308-1322 (1995).
Shaw, A.C., et al., "Activated ras Signals Developmental Progression of Recombinase-Activating Gene (RAG)-Deficient Pro-B Lymphocytes," *J. Exp. Med.*, 189(1): 123-129 (1999).
Stewart, T.A., et al., "Human (β-Globin Gene Sequences Injected into Mouse Eggs, Retained in Adults, and Transmitted to Progeny," *Science*, 217: 1046-1048 (1982).
Takizawa, J., et al., "Expression of the TCL1 Gene at 14q32 in B-Cell Malignancies but not in Adult T-Cell Leukemia," *Jpn. J. Cancer Res.*, 89: 712-718 (1998).
Thick, J., et al., "Expression of Either the TCL1 Oncogene, or Transcripts from its Homologue MTCP1/c6.1(b), in Leukaemic and Non-Leukaemic T Cells from Ataxia Telangiectasia Patents," *Oncogene*, 12: 379-386 (1996).
Virgilio, L., et al., "Identification of the TCL1 Gene Involved in T-Cell Malignancies," *Proc. Natl. Acad. Sci. USA*, 91(26): 12530-12534 (1994).
Virgilio, L., et al., "Deregulated Expression of *TCL1* Causes T Cell Leukemia in Mice," *Proc. Natl. Acad. Sci. USA*, 95: 3885-3889 (1998).
Wagner, E.F., et al., "The Human β-Globin Gene and a Functional Viral Thymidine Kinase Gene in Developing Mice," *Proc. Natl. Acad. Sci. USA*, 78(8): 5016-5020 (1981).
Wagner, T.E., et al., "The Possibility of Transgenic Livestock," *Theriogenology*, 21(1): 29-45 (1984).
Wall, R.J., "Transgenic Livestock: Progress and Prospects for the Future," *Theriogenology*, 45: 57-68 (1996).
Willis, T.G., et al., "Rapid Molecular Cloning of Rearrangements of the IGHG Locust Using Long-Distance Inverse Polymerase Chain Reaction," *Blood*, 90(6): 2456-2464 (1997).
Nakayama, I., et al., "Activation of the TCL1 Protein in B Cell Lymphomas," *Pathology International* 50:191-199 (2000).
Supplementary European Search Report for European Application No. 03731057 dated Sep. 25, 2007.
Blankenstein, T., et al., "A Retroviral Expression Vector Containing Murine Immunoglobulin Heavy Chain Promoter/Enhancer," *Nucleic Acids Research 16*(22):10939 (1988).
Xu, L., et al., "Replacement of Germ-line ε Promoter by Gene Targeting Alters Control of Immunoglobulin Heavy Chain Class Switching," *Proc. Natl. Acad. Sci. USA 90*:3705-3709 (1993).
Notice of Reasons for Refusal from Japanese Patent Application No. 2004-500567, dated Feb. 24, 2009, 4 pages. (3589.1012-007).
Communication Under Rule 71(3) EPC from European Patent Application No. 03 731 057.0, dated Mar. 17, 2009, 5 pages. (3589.1012-006).

\* cited by examiner

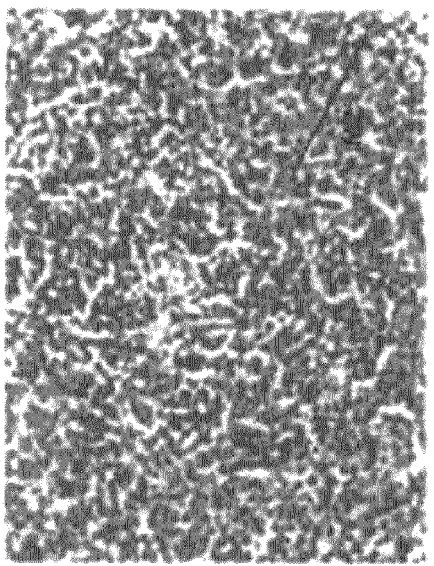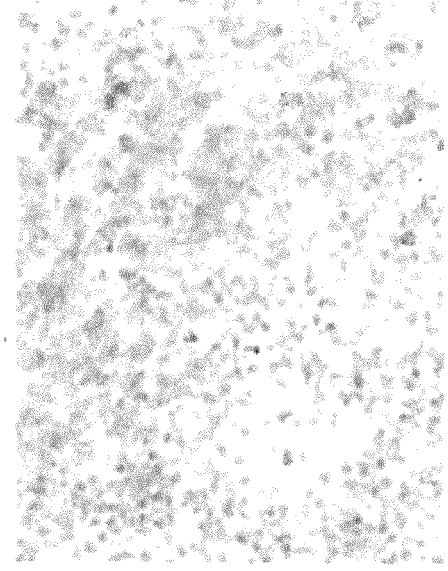
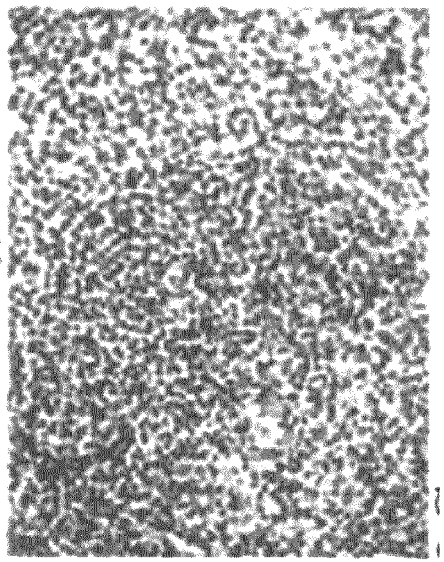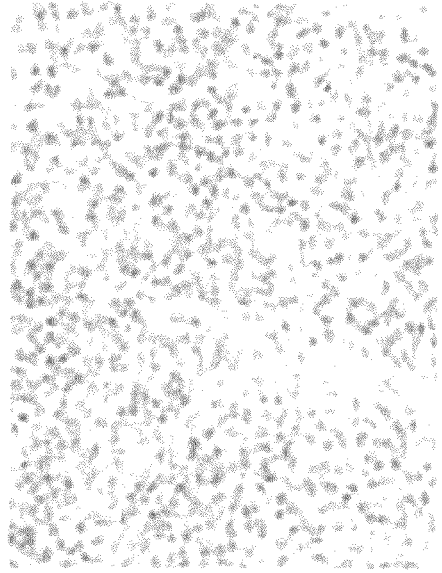
Figure 2B
Figure 2C

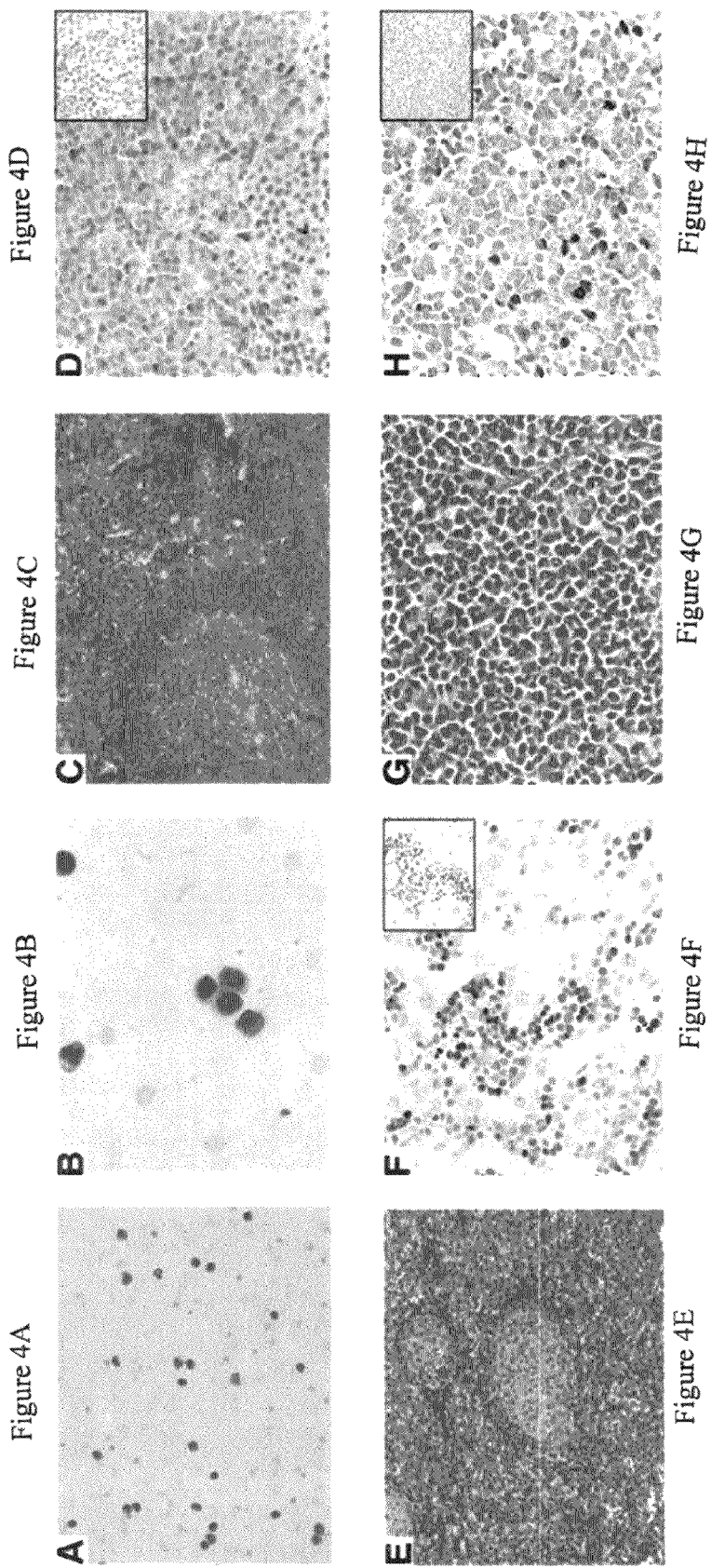

HUMAN CHRONIC LYMPHOCYTIC LEUKEMIA MODELED IN MOUSE BY TARGETED TCL1 EXPRESSION

CROSS-REFERENCE TO RELATED APPLICATIONS

This application is a continuation of U.S. application Ser. No. 10/427,629, filed Apr. 29, 2003, abandoned, which claims priority of U.S. Provisional Application No. 60/376,464, filed on Apr. 29, 2002. The entire teachings of the above applications are incorporated herein by reference.

GOVERNMENT SUPPORT

The present invention was supported by the U.S. National Cancer Institute under Grant Nos. PO1-CA76259 and PO1-CA81534. The government may have certain rights in the invention.

FIELD OF THE INVENTION

The present invention relates to transgenic animal models for lymphoproliferative disorders. More particularly, the present invention relates to transgenic animal models for human B cell chronic lymphocytic leukemia. The present invention also relates to methods of using animal models for testing modalities of treating and preventing lymphoproliferative disorders.

BACKGROUND OF THE INVENTION

B-cell chronic lymphocytic leukemia (B-CLL) is the most common leukemia in the Western world with as many as 10,000 new cases reported each year in the United States (Rai, K. & Patel, D. C. (1995) in Hematology: Basic Principles and Practice, eds. Hoffman et al. (Churchill Livingstone, New York), pp. 1308-1321; Landis, S. H., Murray, T., Bolden, S. & Wingo, P. A. (1998) CA cancer J. Clin. 48, 6-29). Characteristically B-CLL is a disease of elderly people resulting from the progressive accumulation of a leukemic clone that may be derived from a normal CD5+ B lymphocyte (Caligaris-Cappio, F., Gobbi, M., Bofill, M. & Janossy, G. (1982) J. Exp. Med. 155, 623-628). B-CLL has a consistent association with CD5 expression (Caligaris-Cappio, F., Gobbi, M., Bofill, M. & Janossy, G. (1982) J. Exp. Med. 155, 623-628) and while there is still a debate on the role and significance of CD5 expression on B cells, it remains reasonable to consider CD5+ B cells as the normal counterpart of B-CLL (Boumsell, L., Bernard, A.; Lepage, V., Degos, L., Lemerle, J. & Dausset, J., L. (1978) Eur. J. Immunol. 8, 900-904; Kantor, A. B. (1991) Immunol. Today 12, 389-391).

Human hematopoietic malignancies are often caused by chromosome translocations involving either T-cell receptor (TCR) or Immunoglobulin (Ig) loci (Croce, C. M. (1987) Cell 49, 155-156). These chromosome breakpoints juxtapose enhancer elements of TCR and Ig loci to proto-oncogenes, leading to tumor initiation through oncogene deregulation (Dalla-Favera, R., Bregni, M., Erikson, J., Patterson, D., Gallo, R. C. & Croce, C. M. (1982) Proc. Natl. Acad. Sci. USA 79, 7824-7827; ar-Rushdi, A., Nishikura, K., Erikson, R. W., Rovera, G. & Croce C. M. (1983) Science 222, 390-393).

The TCL1 gene, which has been identified at chromosome 14q32.1 (Virgilio, L., Narducci, M. G., Isobe, M., Billips, L. G., Cooper, M. D., Croce, C. M. & Russo, G. (1994) Proc. Natl. Acad. Sci. USA 91, 12530-12534), is commonly activated by inversions or translocations that juxtapose it to a T cell receptor locus at 14q11 or 7q35. The TCL1 gene is involved in chromosomal translocations and inversions in mature T-cell leukemias. These leukemias are classified either as T prolymphocytic leukemias, which occur very late in life, or as T chronic lymphocytic leukemias, which often arise in patients with ataxia telengiectasia (AT) at a young age. TCL1 has been found to be over expressed in sporadic and ataxia telangiectasia associated T-PLL (Narducci, M. G., Stoppacciaro A., Imada, K., Uchiyama, T., Virgilio, L., Lazzeri, C., Croce, C. M. & Russo G. (1997) Cancer Res. 57, 5452-5456; Thick, J., Metacalfe, J. A., Mak, Y-F., Beatty, D., Minegishi, Dyer, M. J. S., Lucas, G. & Taylor, A. M. R. (1996) Oncogene 12, 379-386). In transgenic animals the deregulated expression of TCL1 leads to mature T-cell leukemia, demonstrating the role of TCL1 in the initiation of malignant transformation in T-cell neoplasia. Evidence has been provided that TCL1 is a bona fide oncogene; a transgenic mouse model has been developed in which ectopic expression driven by the lck promoter in the T-cell compartment results in the development of mature T-cell leukemias after a long latency period, in a pattern closely resembling human mature T-cell leukemia (Virgilio, L., Lazzeri, C., Bichi, R., Nibu, K., Narducci, M. G., Russo G., Rothstein, J. L. & Croce C. M. (1998) Proc. Natl. Acad. Sci. USA 95, 3885-3889). In normal T-cells, TCL1 is only expressed at the very early CD4−/CD8− double negative stage, whereas more mature T-cells lack TCL1 expression (Virgilio, L., Narducci, M. G., Isobe, M., Billips, L. G., Cooper, M. D., Croce, C. M. & Russo, G. (1994) Proc. Natl. Acad. Sci. USA 91, 12530-12534). In the B-cell lineage, the product of the TCL1 gene, Tcl1, has been found in pre-B-cells, surface IgM expressing virgin B-cells, mantle cells and germinal center B-cells, whereas it is down-regulated at later stages of B-cell differentiation, i.e. plasma cells (Virgilio, L., Narducci, M. G., Isobe, M., Billips, L. G., Cooper, M. D., Croce, C. M. & Russo, G. (1994) Proc. Natl. Acad. Sci. USA 91, 12530-12534). Interestingly, high levels of Tcl1 have been found in a broad variety of human tumor-derived B-cell lines ranging from pre-B cell to mature B cell and in many cases of B-cell neoplasias (Takizawa, J., Suzuki, R., Kuroda, H., Utsunomiya, A., Kagami, Y., Joh, T., Aizawa, Y., Ueda, R. & Seto, M. (1998) Jpn. J. Cancer Res. 89, 712-718; Narducci, M. G., Pescarmona, E., Lazzeri, C., Signoretti, S., Lavinia, A. M., Remotti, D., Scala, E., Baroni, C. D., Stoppacciaro, A., Croce, C. M., et al. (2000) Cancer Res. 60, 2095-2100). To further elucidate the role of TCL1 in B cell development and in B cell neoplasia, the present inventor generated transgenic mice under the control of a promoter and enhancer whose activity specifically targets expression of the transgene to the B-cell compartment (Shaw, A. C., Swat, W., Ferrini, R., Davidson, L. & Alt, F. W. (1999) J. Exp. Med. 189, 123-129). It is demonstrated herein that Eμ-TCL1 transgenic mice develop a disease resembling human CLL. The mice develop at first a preleukemic state evident in blood, spleen, bone marrow, peritoneal cavity and peripheral lymphoid tissue, developing later a frank leukemia with all the characteristics of CLL. These findings strongly indicate that TCL1 and/or other gene(s) in the TCL1 pathway are responsible for the initiation of human CLL. The animal model described herein thus provides an in vivo model for human B-CLL.

SUMMARY OF THE INVENTION

The present invention is directed, in part, to novel animal models for lymphoproliferative disorders. Specifically, according to an aspect of the invention, there are provided animal models for human B-CLL.

In one embodiment of the invention, a transgenic animal is provided whose genome comprises a nucleic acid construct or transgene comprising at least one transcriptional regulatory sequence capable of directing expression to B cells operably linked to a nucleic acid sequence encoding TCL1. In a preferred embodiment of the invention, the transgene comprises a DNA sequence encoding TCL1 which has been placed under the transcriptional control of a $V_H$ promoter and a $Ig_H$-μ enhancer.

In another embodiment of the invention, white blood cells from a transgenic animal exhibiting lymphoproliferation may be transferred to a second animal (which may be a non-transgenic animal), thereby inducing a rapid onset of lymphoproliferative disease in the second "recipient" animal.

According to another embodiment of the invention, potential therapeutic modalities for preventing and/or treating lymphoproliferative disorders may be tested by measuring the anti-lymphoproliferative activity of such modalities in animals produced according to one or more aspects of the invention.

These as well as other important aspects of the invention will become more apparent from the following detailed description.

BRIEF DESCRIPTION OF THE DRAWINGS

The application file contains at least one drawing executed in color. Copies of this patent application publication with color drawings will be provided by the Office upon request and payment of the necessary fee.

FIGS. 2A-2E show the characterization of Eμ-TCL1 mice. (a) Correlation between IgM and CD5 expression in single cell suspensions from bone marrow, spleen and peritoneal cavity in transgenic animals and a non-TG littermate. (b) Hematoxylin and eosin-stained spleen of mouse showing an expanded marginal zone (MZ) in Eμ-TCL1 animals. (c) Immunodetection of Tcl1 protein in lymphoid cells of the MZ. (d) Cell cycle analysis on IgM and CD5 subsets of cells by PI-labeling. (e) Cell proliferation analysis by BrdU incorporation.

FIGS. 4A-4H show histopathological analyses of the Eμ-TCL1 mice. (a) Blood smear stained with Wright Giemsa showing an increased number of circulating lymphocytes. (b) High magnification of the blood smear. (c) Histology of spleen, liver (e) and cervical lymph node (g) after hematoxylin-eosin staining. (d) Immunodetection of Tcl1 protein in spleen, liver (f) and cervical lymph node (h). Insets: negative controls in which the primary antibody has been omitted.

DETAILED DESCRIPTION OF ILLUSTRATIVE EMBODIMENTS

Figure 1A:
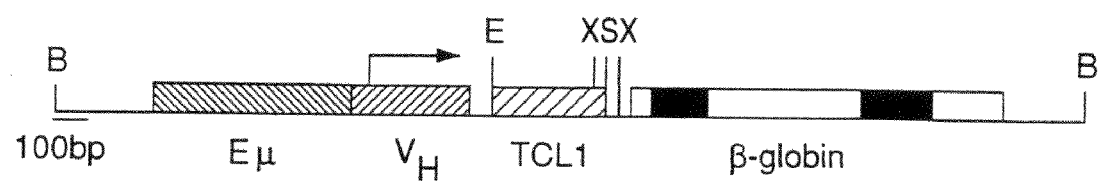
FIGS. 1A-1D illustrate the production of Eμ-TCL1 transgenic mice. (a) Schematic representation of the construct used to generate the mice. Restriction sites: X, XhoI; S, SalI; E, EcoRV; B, BssHII. (b) Southern blot analysis of DNA isolated from the tails of the first transgenic progeny for both founders and non-TG control. (c) Immunoblot analysis on protein extracts from transgenic (F3 and F10) and non-transgenic (C=control) mouse tissues. 697=pre-B leukemic cell line 697 which expresses high levels of Tcl1 protein (9). (d) TCL1 expression on gate subsets of splenic B cells. The upper panel refers to the F3 progeny, the lower panel shows the F10 progeny (Blue=transgenic (TG), Red=non-transgenic (Non-TG)).

As employed above and throughout the disclosure, the following terms, unless otherwise indicated, shall be understood to have the following meanings.

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced nucleic acid molecule may be integrated within a chromosome, or it may be extra-chromosomally replicating DNA. Transgenic animals may include, but are not limited to, those animals in which the genetic information was introduced into a germ line cell, thereby conferring the ability to transfer the information to offspring. If such offspring in fact possess some or all of that information, then they, too, are transgenic animals.

"Anti-lymphoproliferative activity" refers to any activity which inhibits, prevents, and/or destroys the growth of any neoplasms associated with a lymphoproliferative disorder.

As used herein, the term "expanded population of CD5+ B cells" refers to a population of B cells in an experimental animal that represents an increase in the number of CD5+ B cells and/or the proportion of CD5+ B cells relative to other subtypes of B cells, as compared to that of a control animal, as demonstrated, for example, herein in Example 2.

The term "enhancer" is used according to its art-recognized meaning. It is intended to mean a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

"Lymphoproliferative" refers to that which pertains to or is characterized by proliferation of the cells of the lymphoreticular system; the term is generally used to refer to a group of malignant neoplasms. "Lymphoreticular" refers to the cells or tissues of both the lymphoid and reticuloendothelial systems. "Lymphoproliferative disorder" (or "lymphoproliferative disease" or "lymphoproliferative condition") refers to one of a group of malignant neoplasms arising from cells related to the common multipotential, primitive lymphoreticular cell that includes, among others, the lymphocytic, histiocytic, and monocytic leukemias, multiple myeloma, plasmacytoma, Hodgkin's disease, all lymphocytic lymphomas, and immunosecretory disorders associated with monoclonal gammopathy. As used herein, "lymphoproliferative disorder", "lymphoproliferative disease" or "lymphoproliferative condition" may also refer to a physiological state in which the proliferation, multiplication and/or accumulation of cells of the lymphoreticular system is altered relative to a normal or control animal, but the affected animal does not yet necessarily exhibit symptoms of one of the neoplasms described above. As used herein, a "preleukemic" state refers to such a lymphoproliferative condition which precedes the development of overt symptoms of leukemia.

"Neoplasia" refers to the formation of a neoplasm, i.e., the progressive multiplication of cells under conditions that generally would not elicit, or would likely cause cessation of, multiplication of normal cells.

The term "promoter" is used according to its art-recognized meaning. It is intended to mean the DNA region, usually upstream to the coding sequence of a gene or operon, which binds RNA polymerase and directs the enzyme to the correct transcriptional start site.

"Therapeutic modality" refers to any means of treating and/or preventing a given disease, condition or disorder.

The term "transcriptional regulatory sequence" is used according to its art-recognized meaning. It is intended to mean any DNA sequence which can, by virtue of its sequence, cause the linked gene to be either up- or down-regulated in a particular cell. In the case of a promoter, the promoter will generally be adjacent to the coding region. In the case of an enhancer, however, an enhancer may function at some distance from the coding region such that there is an intervening DNA sequence between the enhancer and the coding region.

"Transgene" refers to a nucleic acid sequence introduced into one or more cells of a non-human animal by way of human intervention such as by way of the methods described below.

The introduced genetic information may be foreign to the species of animal to which the recipient belongs, foreign only to the particular individual recipient, or genetic information already possessed by the recipient. In the last case, the introduced genetic information may be differently expressed compared to the native endogenous gene.

To direct expression of the genetic information, which may include a DNA sequence encoding a particular protein (or "coding region"), the coding region of interest may be coupled to at least one transcriptional regulatory sequence in a functional manner. Transcriptional regulatory sequences may be used to increase, decrease, regulate or designate to certain tissues or to certain stages of development the expression of a gene. The transcriptional regulatory sequences need not be naturally occurring sequences.

To produce transgenic animals, any method known in the art for introducing a recombinant construct or transgene into an embryo, such as, for example, microinjection, cell gun, transfection, liposome fusion, electroporation, and the like, may be used. However, the most widely used method for producing transgenic animals, and the method preferred according to the present invention, is microinjection, which involves injecting a DNA molecule into the male pronucleus of fertilized eggs (Brinster et al, 1981; Costantini et al, 1981; Harbers et al, 1981; Wagner et al, 1981; Gordon et al, 1976; Stewart et al, 1982; Palmiter et al, 1983; Hogan et al, 1986; U.S. Pat. Nos. 4,870,009; 5,550,316; 4,736,866; 4,873,191).

The above methods for introducing a recombinant construct/transgene into mammals and their germ cells were originally developed in the mouse. These methods were subsequently adopted for use with larger animals, including livestock species (WO 88/00239, WO 90/05188, WO 92/11757; and Simon et al, 1988). Microinjection of DNA into the cytoplasm of a zygote can also be used to produce transgenic animals.

The present invention is not limited to any one species of animal, but provides for any appropriate non-human vertebrate species. For example, while mouse is a preferred vertebrate species for producing transgenic animals, other non-limiting examples including guinea pigs, rabbits, pigs, sheep, etc., may be suitably used. The success rate for producing transgenic animals by microinjection is highest in mice, where approximately 25% of fertilized mouse eggs into which the DNA has been injected, and which have been implanted in a female, will develop into transgenic mice. A lower success rate has been achieved with rabbits, pigs, sheep and cattle (Jaenisch, 1988; Hammer et al, 1985 and 1986; Wagner et al, 1984).

A nucleic acid molecule is said to be "capable of expressing" or "capable of directing expression of" a protein if it contains nucleotide sequences which contain transcriptional and translational regulatory information, and such sequences are "operably linked" to nucleotide sequences which encode the protein. An operable linkage is a linkage in which regulatory nucleic acid sequences and the nucleic acid sequence sought to be expressed are connected in such a way as to permit gene expression. The regulatory regions needed for gene expression in general may include, for example, transcriptional regulatory sequences such as, for example, a promoter region, as well as DNA sequences which, when transcribed into RNA, will signal the initiation of protein synthesis. Such regions will normally include those 5'-non-coding sequences involved with initiation of transcription and translation. A promoter region would be operably linked to a DNA sequence if the promoter were capable of effecting transcription of that DNA sequence. Thus, in one embodiment of the present invention, a sequence encoding TCL1 is operably linked to transcriptional regulatory sequences directing expression to B cells, to generate a recombinant construct or "transgene" that is then introduced into a fertilized egg.

The methods for evaluating the presence of the introduced transgene as well as its expression are readily available and well-known in the art. Such methods include, but are not limited to, DNA (Southern) hybridization to detect the exogenous DNA, polymerase chain reaction (PCR), polyacrylamide gel electrophoresis (PAGE) and blots to detect DNA, RNA or protein.

B-CLL is the most common leukemia in humans and its pathogenesis is still unknown. Transgenic mice in which the expression of TCL1 was targeted to B cells develop a lymphoproliferative disease closely resembling human CLL. The results provided herein strongly indicate that TCL1 and/or other gene(s) in the TCL1 pathway are responsible for the initiation of human B-CLL. Herein is provided, according to an aspect of the invention, an animal model which may be used to investigate the mechanisms underlying the initiation and progression of human B-CLL. This animal model may also be used in the development and testing of novel therapeutic modalities useful against B-CLL, as well as therapeutic modalities useful against other lymphoproliferative disorders.

One aspect of the invention relates to transgenic animals that express TCL1 in B cells. In one embodiment of the invention, a transgenic animal is provided whose genome comprises a nucleic acid construct or transgene comprising at least one transcriptional regulatory sequence capable of directing expression to B cells operably linked to a nucleic acid sequence encoding TCL1. In a preferred embodiment of the invention, the transgene comprises a DNA sequence encoding TCL1 which has been placed under the transcriptional control of a $V_H$ promoter and a $Ig_H$-μ enhancer. In such animals, TCL1 expression is directed to immature and mature B cells. In one embodiment of the invention, the transgenic animals are mice which develop an expanded population of B cells that express the cell surface marker CD5. As the animals age, they develop lymphocytic leukemia involving CD5+ B cells. This condition exhibits characteristics of human B-CLL.

In another embodiment of the invention, white blood cells from a transgenic animal exhibiting lymphoproliferation may be transferred to a second animal (which may be a non-transgenic animal), thereby inducing a rapid onset of lymphoproliferative disease in the second "recipient" animal.

According to another embodiment of the invention, potential therapeutic modalities for preventing and/or treating lymphoproliferative disorders may be tested by measuring the anti-lymphoproliferative activity of such modalities in animals produced according to one or more aspects of the invention. Such activity may be assessed by measuring the capacity of a potential therapeutic modality to inhibit, prevent, and/or destroy one or more of the symptoms or indications of lymphoproliferative disease exhibited by transgenic animals produced according to one embodiment of the invention and/or in "recipient" animals produced according to another embodiment of the invention as described above. Such therapeutic modalities, such as, for example, chemical compounds, will be formulated in accordance with known methods to produce pharmaceutically acceptable compositions. Such compositions may be administered to patients in a variety of standard ways.

EXAMPLES

The invention is further demonstrated in the following examples. All of the examples are actual examples. The examples are for purposes of illustration and are not intended to limit the scope of the present invention.

Materials and Methods

Eμ-TCL1 Transgenic Mice

A 350-bp fragment possessing the entire human TCL1 coding region was generated by PCR and cloned into the EcoRV and SalI sites of the pBSVE6BK (pEμ) plasmid containing a mouse VH promoter (V186.2) and the IgH-μ enhancer along with the 3' untranslated region and the poly (A) site of the human β-globin gene. The construct containing TCL1 free from vector sequences was injected into fertilized oocytes from B6C3 animals. Mice were screened for the presence of the transgene by Southern blot analysis on tail DNAs digested with XhoI. Blots were hybridized with the same BssHII DNA fragment used to inject the oocytes. Two founders were obtained (F3 and F10) and bred. Transgenic heterozygote mice issued from these founders were studied and compared with nontransgenics siblings raised in identical conditions. Genotyping was performed on tail DNAs by Polymerase chain reaction (PCR).

Western Blot Analysis

Cell proteins were extracted with NP-40 lysis buffer, quantified using the BCA kit (Pierce), size fractionated on 15% Tris-glycine SDS-PAGE gels and electrotransferred onto nitrocellulose (Immobilon-P, Millipore). The membrane was blocked overnight in 10% nonfat dried milk in PBST (phosphate-buffered saline (PBS): 7.6 g/L NaCl, 0.7 g/L Na2PO4, 0.2 g/L KPO4 and 0.1% Tween 20). Expression was detected with the MoAb 27D6/20 for human Tcl1 protein (14) according to ECL protocol (Amersham). Ponceau-S staining was employed to verify equivalent protein loading.

Cell Preparations

Bone marrow cells were isolated by flushing the cavities of the femur and tibia with ice cold staining medium (Deficient RPMI, Irvine Scientific) containing 10 mM HEPES, 0.1% NaN3, 3% FCS. Spleens were dissociated in staining medium between two frosted slides. Peritoneal cells were removed by injection of 10 ml of staining medium into the peritoneal cavity following by withdrawal of the peritoneal exudates. Erythrocytes were lysed by brief treatment with 0.165 M ammonium chloride and the cells then washed in staining medium.

White Blood Cell Preparation

Blood was collected from the cavernous sinus with a capillary tube in a tube coated with EDTA (Becton Dickinson). Smears were immediately prepared and stained with May Grünwald Giemsa. Full counts were made on a cell counter (Beckman). For immunofluorescence staining cells were treated with 0.165 M ammonium chloride to eliminate red cells and washed in staining medium.

Immunofluorescence Analysis and Cell Sorting

Single cell suspension of the indicated cell type were prepared and stained for surface expression as described previously (Hardy, R. R., Carmack, C. E., Shinton, S. A., Kemp, J. D. & Hayakawa, K. (1991) *J. Exp. Med.* 173, 1213-1225). Cells were stained for surface expression of IgM and CD5, then fixed and permeabilized using the Fix&Perm kit (CalTag) and stained for expression of Tcl1 using a PE-labeled anti-Tcl1 monoclonal antibody 27D6/20 (Narducci, M. G., Pescarmona, E., Lazzeri, C., Signoretti, S., Lavinia, A. M., Remotti, D., Scala, E., Baroni, C. D., Stoppacciaro, A., Croce, C. M., et al. (2000) *Cancer Res.* 60, 2095-2100). IgM/CD5 distributions were gated as indicated and histograms of the Tcl1 staining determined. Plots were done with FlowJo software (Tree Star, Inc.). Exclusion of propidium iodide was used to eliminate dead cells and samples shown were also gated by forward and right angle scatter to exclude non-lymphoid cells and debris. Flow cytometry and sorting was done on a dual-laser dye-laser FACStarPLUS equipped with detectors for 5 colors immunofluorescence. Samples were held on ice during sorting. Preparation of labeled reagents has been described previously (Hardy, R. R. (1986) in: *The Handbook of Experimental Immunology* 4th Edition, eds. Weir, D. M., Herzenberg, L. A., Blackwell, C. C. & Herzenberg L. A. (Blackwell scientific Pub. Ltd., Edinburgh), pp. 31.1-31.12).

Analysis of VH11 Sequences

Cells were stained for IgM/CD5 expression and $1\times10^5$ IgM+CD5+ cells were sorted directly into lysis/denaturation buffer. RNA and cDNA were prepared as described previously (Li, Y. S., Wasserman, R., Hayakawa, K. & Hardy, R. R. (1996) *Immunity* 5, 527-535) and a VH11-Cμ fragment was amplified using a VH11 leader and Cμ primer using Pfu polymerase and PCR. The amplified material was cloned using the TOPO TA cloning kit (Invitrogen) following manufacturer's instruction. Colonies with insert were expanded, plasmid DNA isolated and sequenced using an ABI 377 automated sequencer as described previously (Hardy, R. R., Carmack, C. E., Li, Y. S. & Hayakawa, K. (1994) *Immunol. Rev.* 137, 91-118).

Analysis of Cell Cycle

For Propidium Iodide (PI) staining, $10^5$ cells were sorted directly into ice cold 95% ethanol, nuclei were pelleted, then resuspended in PI-labeling solution (1 mg/ml RNAse A, 20 µg/ml propidium iodide in PBS containing 0.0.1% NP40). After 30 minutes cells were analyzed for PI fluorescence on a FACScan using doublet discrimination gating.

Analysis of Cell Proliferation

Mice were injected intraperitoneally with 5-Bromodeoxyuridine (BrdU) in PBS at a dose of 50 µg per gram of body weight daily for four days. Mice were sacrificed and cells were stained for expression of IgM and CD5, then sorted to obtain the indicated populations. 5×105 cells were fixed and permeabilized, then treated with DNAse in acid buffer and stained with an anti-BrdU monoclonal antibody labeled with FITC. Samples were analyzed on a FACScan for BrdU staining.

Analysis of IgH Gene Rearrangement

Southern blots of DNA digested with EcoRI and StuI were prepared following conventional methods and hybridized with a 32P-labeled DNA probe PJ3 representing the JH4 region of the IgH locus.

The probe was synthesized by PCR amplification from mouse DNA with primers F2 (5'-TGTGGTGACATTAGAACTGAAGTA-3') (SEQ ID NO:1) and R1 (5'-CAAGATTAGTCTGCAATGCTCAGA-3') (SEQ ID NO:2).

Long Distance Inverse PCR (LDI-PCR)

High molecular weight DNA was digested with StuI. LDI-PCR was performed as described (Willis, T. G., Jadayel, D. M., Coignet, L. J. A., Abdul-Rauf, M., Treleaven, J. G., Catovsky, D. & Dyer, M. J. S. (1997) *Blood* 90, 2456-2464). Primers designed within the mouse JH and IGH enhancer regions were used to amplify the purified DNA and the gel-purified products were ligated into pCR 2.1-TOPO vector (Invitrogen). Plasmids containing the correct size insert were sequenced using an ABI 377 automated sequencer and compared with the Genbank database using the BLAST program (http://www.ncbi.nlm.nih.gov/BLAST/). The VH, DH and JH segments were identified using the Genbank database.

Histopathology and Immunohistochemistry

Animals were autopsied and tissues were fixed in 10% buffered formalin and embedded in paraffin. Sections were stained with hematoxylin and eosin according to standard protocols and analyzed by mouse pathologists (University of Missouri, Research Animal Diagnostic Laboratory). Immunohistochemistry was performed on representative sections. For the dewaxing step the sections were heated for 1 h at 55° C. followed by a rehydratation steps through a graded ethanol series and distilled water, immersed in PBS then treated with 0.1% trypsin solution in Tris buffer for 30 min at 37° C. Endogenous peroxidase was blocked with 10% normal serum. The 27D6/20 MoAb specific for recombinant human Tcl1 protein (14) was used as a primary antibody and the immunohistochemical staining was performed by using streptoavidin-biotin peroxidase labeling method according to the manufacturer's instructions (Histomouse-SP kit, Zymed).

Example 1

Production and Characterization of Eµ-TCL1 Transgenic Mice

Figure 1C:
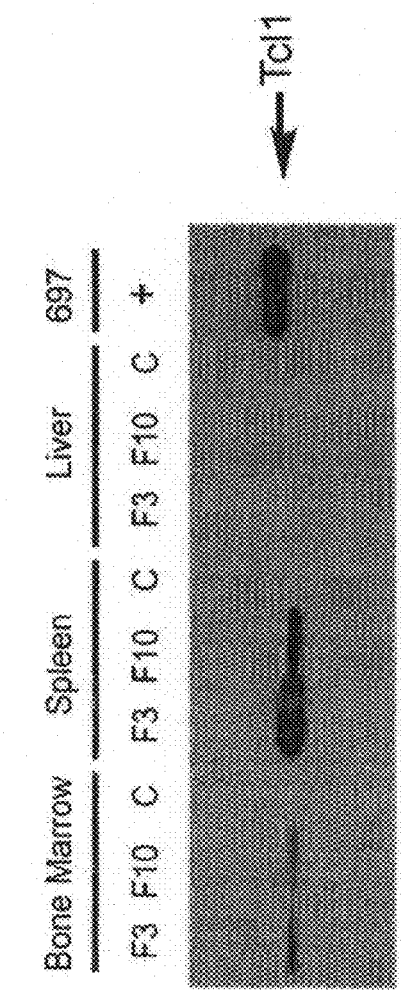
Figure 1B:
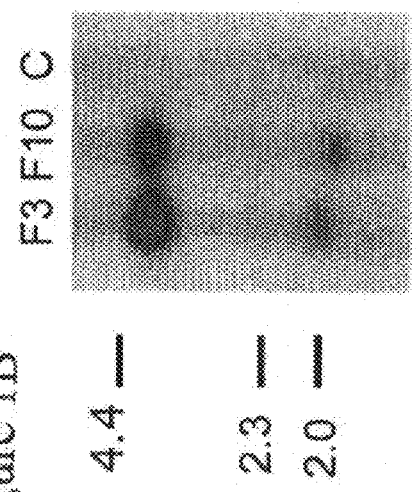
Figure 1D:
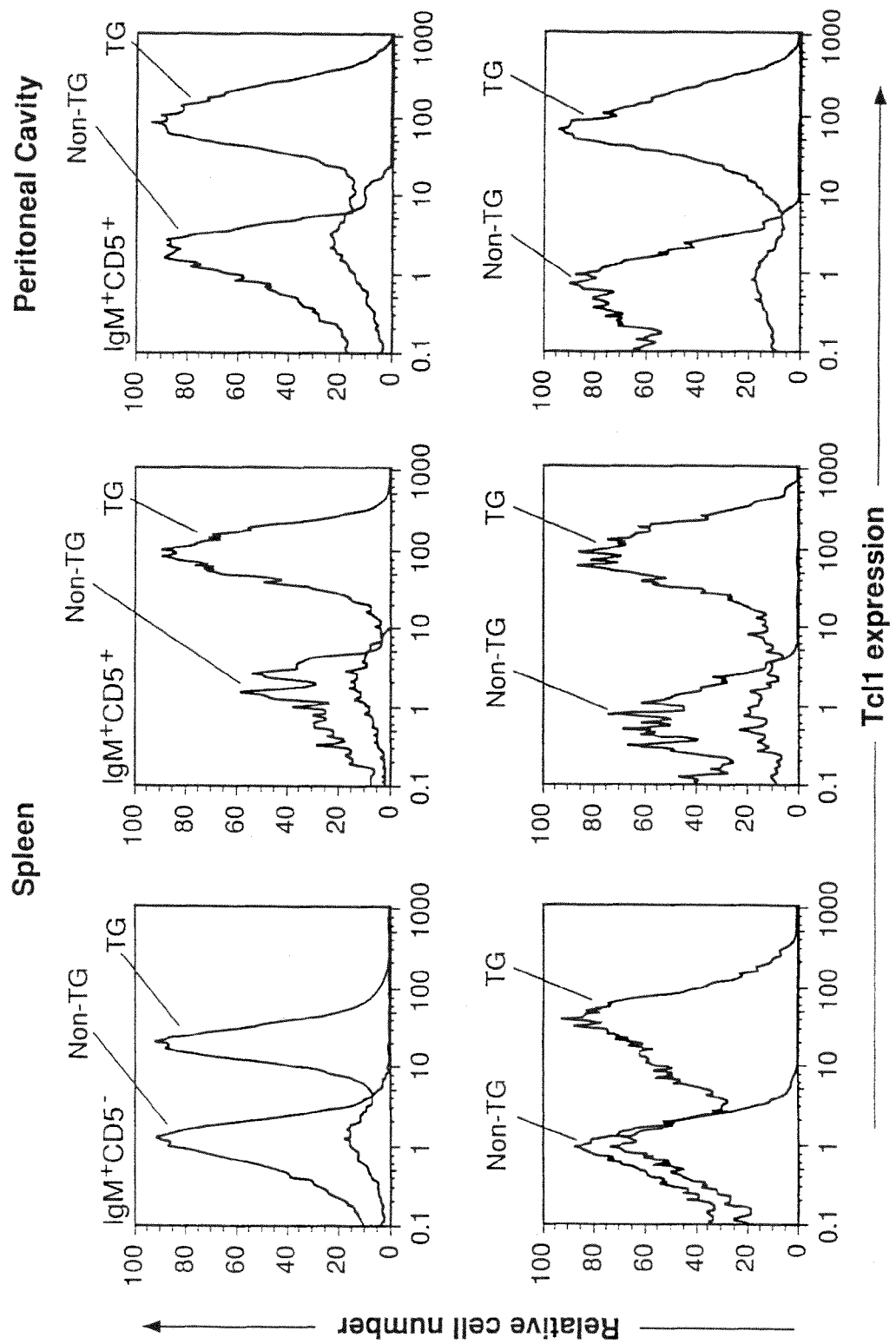

Transgenic mice were generated in which the expression of TCL1 was under the control of a VH promoter-IgH-Eµ enhancer whose activity specifically targets expression of the transgene to immature and mature B-cells (Shaw, A. C., Swat, W., Ferrini, R., Davidson, L. & Alt, F. W. (1999) *J. Exp. Med.* 189, 123-129) (FIG. 1*a*). Two transgenic founders on a B6C3 background, designated F3 and F10, were generated and bred to establish two transgenic lines (FIG. 1*b*). The expression of the transgene in each was evaluated by western blot of total protein extracted from spleen, bone marrow and liver of 3-month-old mice, using a monoclonal antibody specific for human Tcl1 protein (, M. G., Pescarmona, E., Lazzeri, C., Signoretti, S., Lavinia, A. M., Remotti, D., Scala, E., Baroni, C. D., Stoppacciaro, A., Croce, C. M., et al. (2000) *Cancer Res.* 60, 2095-2100). The two transgenic lines expressed Tcl1 in spleen and bone marrow while no expression was detected in liver or in non-transgenic siblings (FIG. 1*c*). Fluorescence-activated cell sorting (FACS) was also used to investigate the distribution of TCL1 expression on gated subsets of B cells derived from spleen and peritoneal cavity of 3-month-old mice, in both transgenic lines. The combination of cell surface markers with intracellular detection of Tcl1 revealed a high level of TCL1 expression in normal resting B cells with a 2.5-fold higher level in the CD5+ cells (FIG. 1*d*).

Example 2

Phenotypic Analyses of Eµ-TCL1 Transgenic Mice

As demonstrated below, flow cytometric analysis revealed a markedly expanded CD5+ population in the peritoneal cavity of Eµ-TCL1 mice starting at two months of age that became evident in the spleen by 3-5 months and in the bone marrow by 5-8 months. Analysis of immunoglobulin gene rearrangements indicated monoclonality or oligoclonality in these populations suggesting a preneoplastic expansion of CD5+ B cell clones.

Figure 2A:
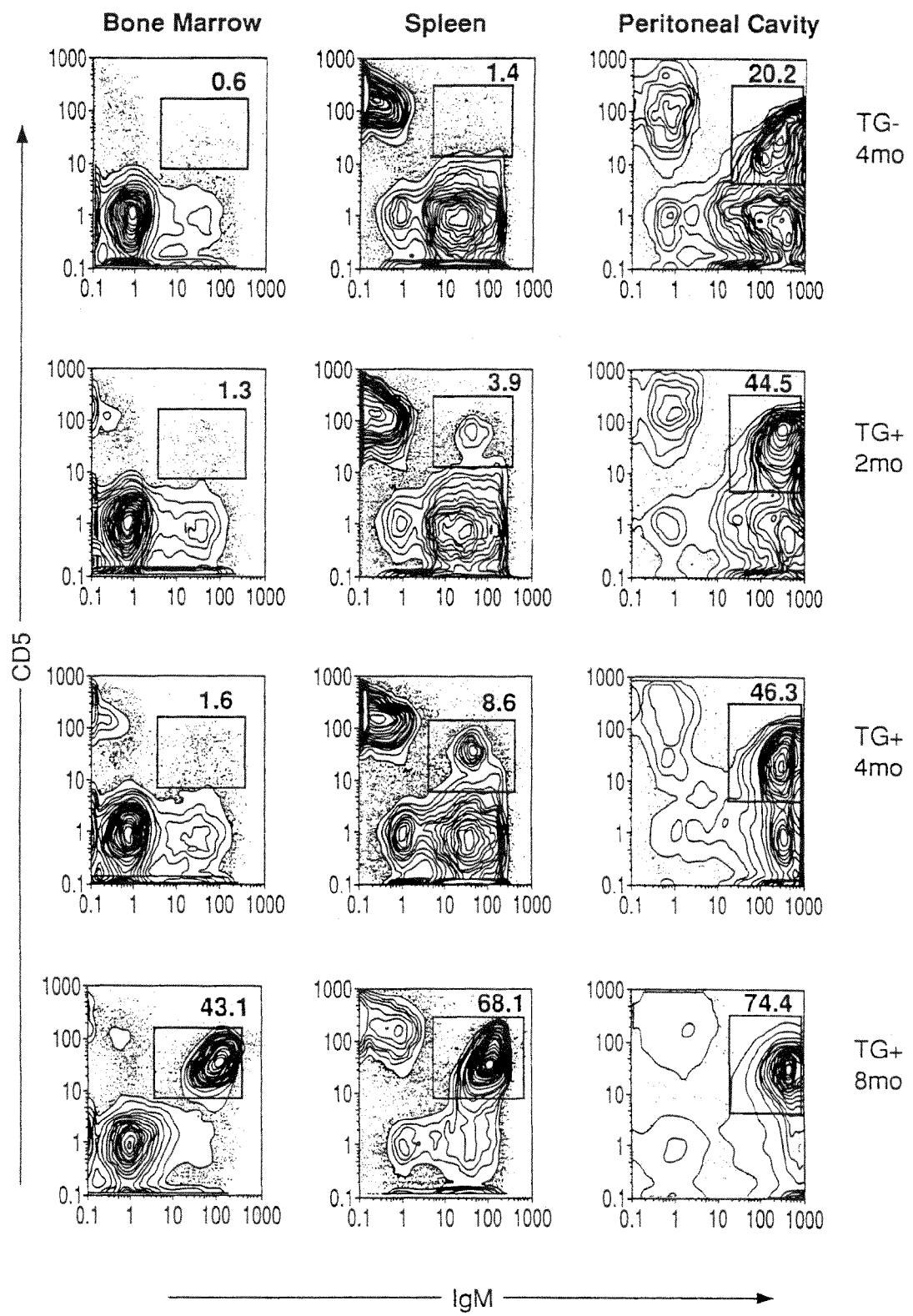

The Immunophenotyping of Eµ-TCL1 Transgenic Mice Reveals an Expanded CD5+/IgM+ Population Flow cytometry was used to monitor the immunophenotypic profile of peripheral blood lymphocytes (PBLs) from mice of these two lines between one and nine months of age. The results revealed the presence of a B220low/IgM+ population that was detected starting at six months of age in 100% of the transgenic mice, but in the absence of any sign of disease. A normal distribution of B cell populations was found in the non-transgenic controls. T cell subsets were normal and identical between transgenic animals and their littermate controls. Eµ-TCL1 transgenic mice were further characterized in order to identify the B cell subsets affected. The expanded B220low/IgM+ population was found to co-express CD5 and Mac-1/CD11b. This result suggested that the Eµ-TCL1 transgenic mice had an expanded population of CD5+/B1 cells in peripheral blood, where such cells are normally infrequent (Kantor, A. B. & Herzenberg, L. A. (1993). *Annu. Rev. Immunol.* 11, 501-538). In mice, CD5 is a pan-T cell surface marker that is also present on a subset of B-lymphocytes that appear during fetal/neonatal time, and whose development appears quite distinct from the majority of B cells (Hardy, R. R., Carmack, C. E., Li, Y. S. & Hayakawa, K. (1994) *Immunol. Rev.* 137, 91-118; Hayakawa, K. & Hardy, R. R. (1988) *Annu. Rev. Immunol.* 6, 197-218). CD5 is also frequently expressed on murine B cell lymphomas and leukemias (Lanier, L. L., Warner, N. L., Ledbetter, J. A. & Herzenberg, L. A. (1981) *J. Exp. Med.* 153, 998-1003; Phillips, J. A., Mehta, K., Fernandez, C. & Raveché, E. S. (1992) *Cancer Res.* 52, 437-443). A group of animals was analyzed at 2, 4 and 8 months of age to assess the expansion of the CD5+//IgM+ population in bone marrow, spleen and peritoneal cavity. FACS analysis revealed a phenotypically homogeneous population markedly expanded in the peritoneal cavity of the transgenic mice starting at two months of age (44%) that became evident in spleen (8.6%) by 4 months and bone marrow by 8 months (43%) (FIG. 2a).

Histological and Immunocytochemical Analysis of the Transgenic Mice

Eight-month-old transgenic mice presented a slightly enlarged spleen, 1.5-fold compared to littermate controls and moreover a very high cellularity in the peritoneal cavity, ranging between 50- to 100-fold increased. Histopathology of enlarged spleens of Eμ-TCL1 mice demonstrated a consistent increase in the size of the marginal zone (MZ) (FIG. 2b). Immunostaining of lymphoid cells in the white pulp of the spleen showed Tcl1 staining more intensely in the MZ. As expected no immunostaining was observed in the spleen of littermate controls (FIG. 2c). Interestingly, the anatomical localization of the expanded CD5+ cells was in the MZ whereas they did not have the precise phenotype of typical MZ B cells, i.e. not CD21-high but rather CD21-low, like a normal CD5+ B cell (Chen, X., Martin, F., Forbush, K. A., Perlmutter, R. M. & Kearney, J. F. (1997) *Int. Immunol.* 9, 27-41). The histological analysis of other tissues from the same animals, including thymus, liver, kidney and intestine, did not reveal any pathologic alteration (not shown).

Analysis of VH11 Sequences in the Expanded CD5+ Population

The increased frequency of CD5+ B cells in these transgenic mice could represent either the induction of CD5 expression on cells normally not CD5+ or else the expansion of normally generated CD5+ B cells. In order to distinguish between alternatives we investigated V gene usage in the expanded cell population. Recurrent expression of certain VHVL combinations is a characteristic feature of normal and neoplastic CD5+ B cells (, R. R., Carmack, C. E., Li, Y. S. & Hayakawa, K. (1994) *Immunol. Rev.* 137, 91-118; Pennell, C. A., Arnold, L. W., Haughton, G. & Clarke, S. H. (1988) *J. Immunol.* 141, 2788-2796). Using antibodies specific for variable regions, we found that one of these combinations, VH11Vk9, was repeatedly represented at 5-10% in the expanded CD5+ B cell population in all mice analyzed, similar to the frequency seen in normal CD5+ B cells (data not shown). Furthermore, analysis of VH11 sequences from sorted IgM+/CD5+ cells from the spleen of a 3-month-old transgenic mouse (Table 1) showed normal VH11 rearrangements with low levels of N-region addition, typical of CD5+ B cells that are predominantly generated fetally/neonatally when levels of TdT are low (Li, Y. S., Hayakawa, K. & Hardy, R. R. (1993) *J. Exp. Med.* 178, 951-960).

TABLE 1

Analysis of $V_H11$ sequences in CD5+ splenic B cells

| Seq. ID | $V_H11$ | N | $D_H$ | N $J_H$ | $D_H$ | $J_H$ |
|---|---|---|---|---|---|---|
| TCL1-4 | TGTATGAGA (SEQ ID NO: 3) | TA | TAGTAGC (SEQ ID NO: 4) | TACTGGTACTTC (SEQ ID NO: 11) | DFL16.1 | $J_H1$ |
| TCL1-11 | TGTATGAGA (SEQ ID NO: 3) | | TATGGTAAC (SEQ ID NO: 5) | TACTGGTACTTC (SEQ ID NO: 11) | DSP2.8 | $J_H1$ |
| TCL1-17 | TGTATGAGA (SEQ ID NO: 3) | | TACGGTAGT AGC (SEQ ID NO: 6) | TACTGGTACTTC (SEQ ID NO: 11) | DFL16.1 | $J_H1$ |
| TCL1-42 | TGTATGAGA (SEQ ID NO: 3) | | TATGGTAAC (SEQ ID NO: 5) | TACTGGTACTTC (SEQ ID NO: 11) | DSP2.8 | $J_H1$ |
| TCL1-44 | TGTATGAGA (SEQ ID NO: 3) | | TATGGTAACTAC (SEQ ID NO: 7) | TACTGGTACTTC (SEQ ID NO: 11) | DSP2.1 | $J_H1$ |
| TCL1-46 | TGTATGAGA (SEQ ID NO: 3) | | TACGGTAGTAGC (SEQ ID NO: 8) | TACTGGTACTTC (SEQ ID NO: 11) | DFL16.1 | $J_H1$ |
| TCL1-47 | TGTATGAGA (SEQ ID NO: 3) | | TATGATGGTTAC (SEQ ID NO: 9) | TACTGGTACTTC (SEQ ID NO: 11) | DSP2.9 | $J_H1$ |
| TCL1-52 | TGTATGAGA (SEQ ID NO: 3) | | TATAGTAAC (SEQ ID NO: 10) | TACTGGTACTTC (SEQ ID NO: 11) | DSP2.X | $J_H1$ |

Figure 2D:
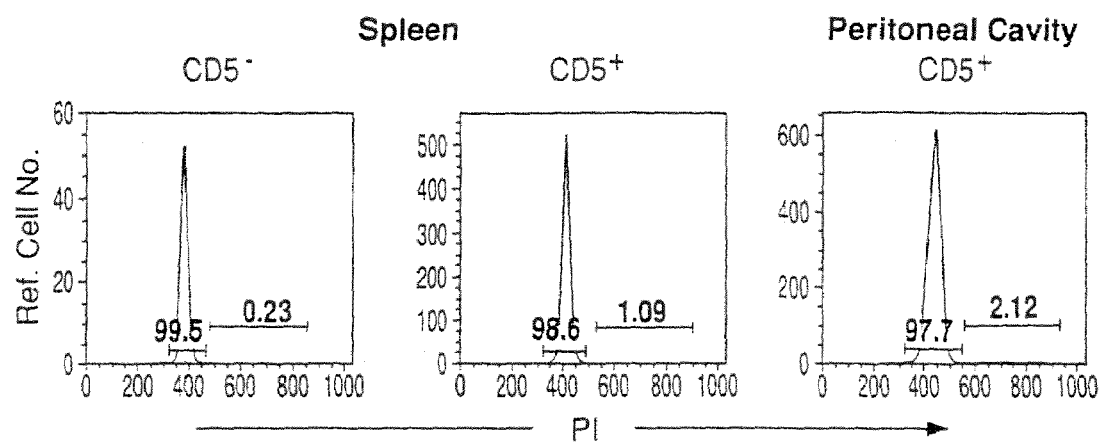
Figure 2E:
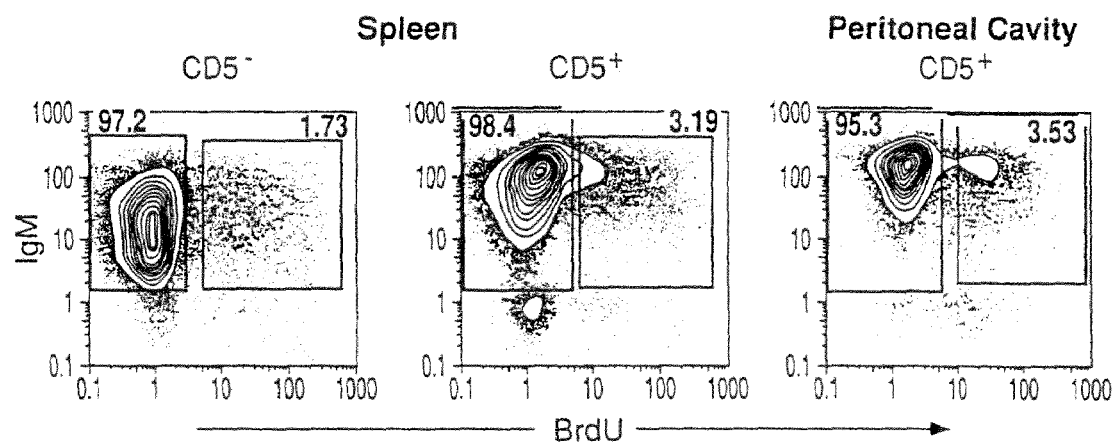

IgM+/CD5+ Populations Are Arrested in the G0/G1 Phase of the Cell Cycle and Do Not Actively Divide Chronic lymphocytic leukemia cells is characterized by a low proliferative activity and by the progressive accumulation of clonal B lymphocytes blocked in the early phases (G0/G1) of the cell cycle (Andreeff, M., Darzynkiewicz, Z., Sharpless, T. K., Clarkson, B. D. & Melamed, M. R. (1980) *Blood* 55, 282-293; Nilsson, K. (1992) in *Chronic Lymphocytic Leukemia: Scientific Advances & Clinical development*, ed. Cheson, B. D. (New York), pp. 33-45). The present inventor investigated the cell cycle distribution and the rate of cell proliferation in spleen and peritoneal cavity of four transgenic mice and four littermate controls at 7 months of age. Detection of DNA content in replicating cells by propidium iodide (PI) labeling and analysis of cell proliferation from the distribution of 5-bromo-2'deoxyuridine (BrdU) incorporation in IgM+CD5+ sorted populations revealed that most of these cells are not actively cycling in the transgenic mice (FIG. 2d,e).

IgH Gene Configuration in Transgenic Mice with the Expanded CD5+ Population

Figure 3A:
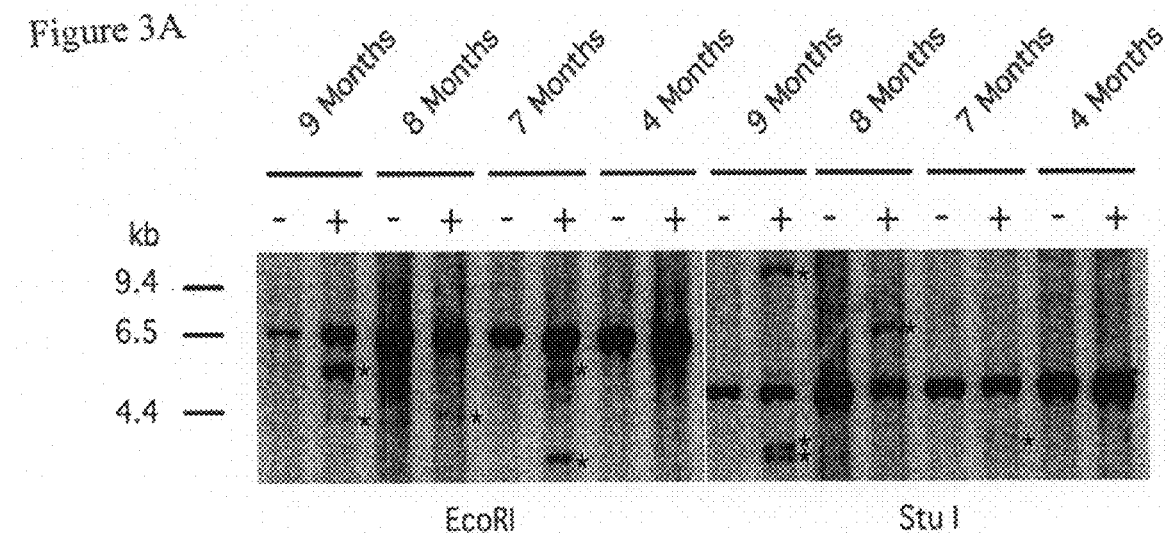
FIGS. 3A-3B show the analyses of IgH gene configuration. (a) IgH gene rearrangements were analyzed by Southern blot on EcoRI and StuI-digested splenocyte DNAs. Transgenic mice (+) of 7, 8 and 9 months show rearranged bands (asterisks). No predominant rearrangement is observed in the youngest mice. Controls (−) are non-TG mice with the genomic 6.5-kb EcoRI and 4.7-kb StuI fragments. (b) Southern blots on DNA isolated from bone marrow, spleen and peritoneal cavity of transgenic mice (#40, #41) with the CD5+/IgM+ expanded population. IgH gene predominant rearrangements were detected in spleen and peritoneal cavity (asterisks). DNA from spleen of non-TG mouse was used as control.
Figure 3B:
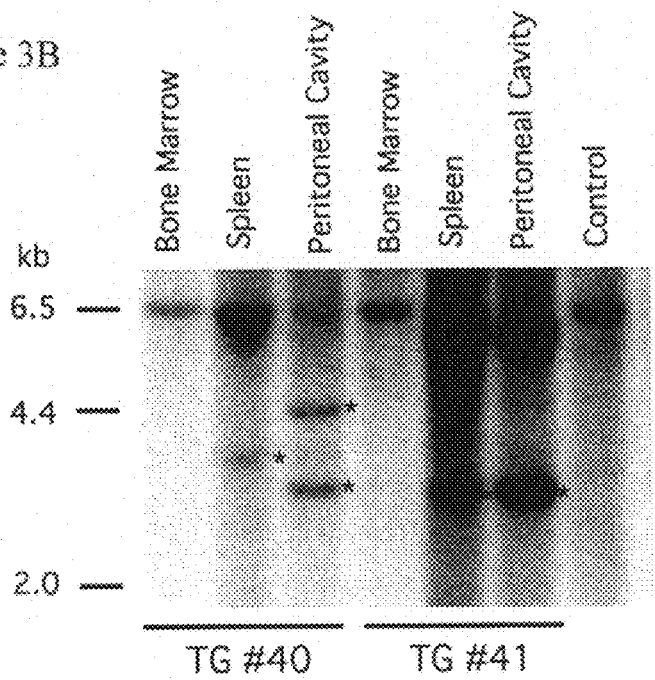

Analysis of Ig gene rearrangement revealed the presence of preleukemic or leukemic clones consistently in Eμ-TCL1 mice over seven months of age. No clonality was observed in the youngest transgenics or in non-transgenic mice (FIG. 3a). The detection of clonal JH rearrangements indicated that there could be a clonal expansion without evidence of disease. Further analysis of Ig gene rearrangement in bone marrow, spleen and peritoneal cavity from 8-month-old mice with a markedly expanded CD5+/IgM+ population showed an identical size JH band detected in spleen and peritoneal cavity, but not bone marrow (FIG. 3b). The clonal JH band was not always shared between spleen and peritoneal cavity; note, for example, mouse # 40 (FIG. 3b), which shows two independent clonal populations, suggesting that multiple independent events may occur in some cases. Clonal rearrangements were subsequently confirmed in some samples by cloning and sequencing the rearranged band using a long-distance inverse polymerase chain reaction (LDI-PCR) (Willis, T. G., Jadayel, D. M., Coignet, L. J. A., Abdul-Rauf, M., Treleaven, J. G., Catovsky, D. & Dyer, M. J. S. (1997) *Blood* 90, 2456-2464). Using this approach, the transgenic mice exhibited additional clonal rearrangements compared to the littermate controls. Table 2 shows sequence data referring to the (+) samples marked as 9m and 8m in FIG. 3a, StuI digested. Some sequences had a low level of N addition, whereas others had a higher level (Table 2), as has been noted in sequence analyses of normal CD5+ B cells (Kantor, A. B., Merrill, C. E., Herzenberg, L. A. & Hillson, J. L. (1997) *J. Immunol.* 158, 1175-1186). The clonal population suggested by Southern blot for the transgenic # 41 (FIG. 3b) in spleen and peritoneal cavity was also confirmed by LDI-PCR (Table 2).

TABLE 2

Results of VDJ rearrangements in selected cases of Eμ-TCL1 transgenic mice

| Mouse | $V_H$ | $D_H$ | $J_H$ | $V_H$ | $D_H$ | $J_H$ |
|---|---|---|---|---|---|---|
| 9m | TACTGTGCCA GA (SEQ ID NO: 12) | aATGGTTAC GA (SEQ ID NO: 15) | CTATGCTATGGACTACTG GGGTCAAGGAACCTCAG TCACCGTCTCCTCA (SEQ ID NO: 19) | Vox-1 | DSP2.6 | $J_H4$ |
| 9m | TACTGTGCCA GA (SEQ ID NO: 12) | ACGGTAGT AGCcct SEQ ID NO: 16) | CTATGCTATGGACTACTG GGGTCAAGGAACCTCAG TCACCGTCTCCTCA (SEQ ID NO: 19) | Vox-1 | DFL16.1 | $J_H4$ |
| 8m | GTCTATTACT GT (SEQ ID NO: 13) | actccccACTA CGGTAGTA GCct (SEQ ID NO: 17) | CTGGTACTTCGATGTCTG GGGC<u>A</u>CAGGGACCACGG TCACCGT<u>C</u>TCCTGA (SEQ ID NO: 20) | V130 | DFL16.1 | $J_H1$ |
| #41 PerC | GCAGGAGAC AGA (SEQ ID NO: 14) | TATGGTTA (SEQ ID NO: 18) | CTGGTACTTCGATGTCTG GGGC<u>A</u>CAGGGACCACGG TCACCGT<u>C</u>TCCTCA (SEQ ID NO: 20) | NC1-A7 | DSP2.6 | $J_H1$ |
| #41 Spleen | GCAGGAGAC AGA (SEQ ID NO: 14) | TATGGTTA (SEQ ID NO: 18) | CTGGTAGTTCGATGTCTGGG GC<u>A</u>CAGGGACCACGGTCAC CGT<u>C</u>TCCTCA (SEQ ID NO: 20) | NC1-A7 | DSP2.6 | $J_H1$ |

Variations from the germline sequence are underlined. N regions are in lowercase.

Example 3

Eμ-TCL1 Mice Developed Lymphocytic Leukemia Upon Aging

Figure 5:
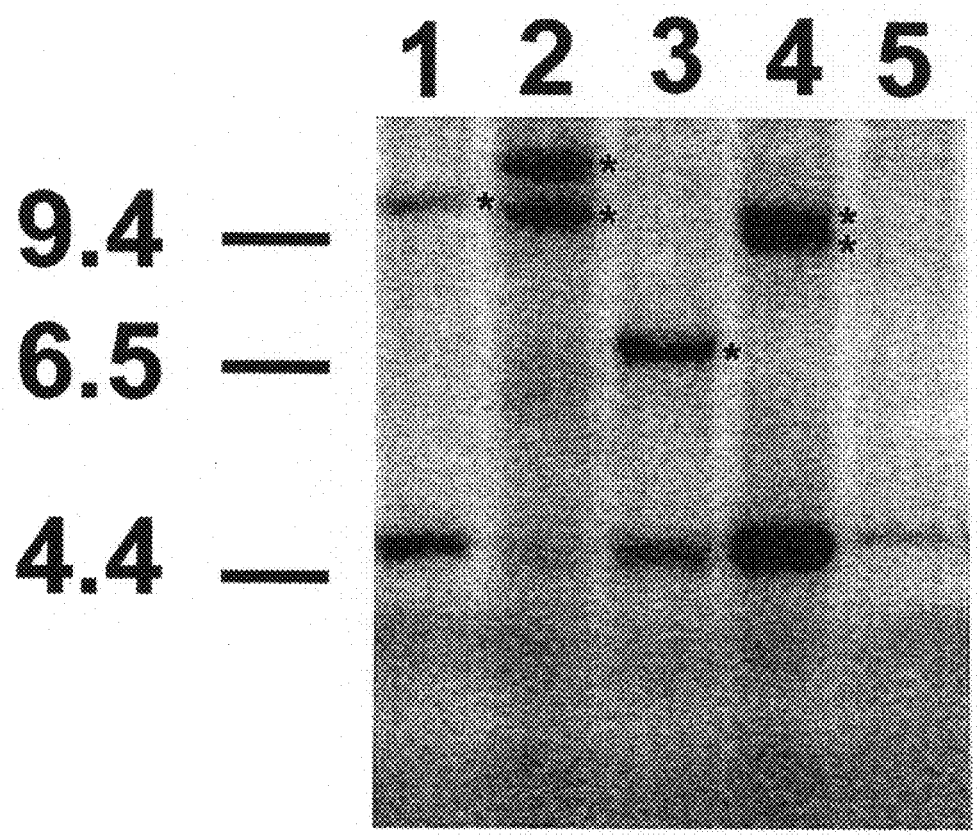
FIG. 5 shows the Southern blot analysis of IgH gene rearrangements in leukemias from transgenic mice. DNAs from leukemic mice and a littermate control were digested with StuI. The strong 4.7-kb bands represent the gene in its germline configuration. Clonal rearrangements are indicated by asterisks. Lanes 1 and 2=leukemic mice from transgenic line F3; lanes 3 and 4=leukemic mice from transgenic line F10; Lane 5=non-transgenic mouse.

Older mice eventually develop a CLL-like disorder resembling human B-CLL The onset of a frank leukemia in the elderly mice provided further evidence of the establishment of a murine model for B-CLL. All mice around the age of 13-18 months became visibly ill and presented with enlarged spleens and livers associated with high white blood cell (WBC) counts. The weight of the transgenic spleens was between 1.5 g and 2.3 g (normal splenic weight was $0.07±0.01$ g) and the mean of the WBC $180.0×10^6$ cells/ml (the mean WBC/ml blood for normal adult mice was $2.8×10^6$ cells/ml). In addition the mice also developed advanced lymphoadenopathy, a hallmark of human CLL. Cytological examination of blood smears showed an increase in circulating lymphocytes with many of them displaying a clumped nuclear chromatin (FIG. 4a,b). The predominant cell type was represented by large lymphoid cells and smudged cells were also present. Histopathological examination demonstrated consistent infiltration of spleen, liver and lymph nodes by small and large lymphocytes (FIG. 4c,e,g). Positive staining for Tcl1 protein was observed primarily in lymphocytes found in these tissues (FIG. 4d,f,h) and flow cytometric analysis confirmed the expansion of the CD5+/IgM+ population in all tissues (data not shown). Clonality was shown by southern blot analysis of DNA isolated from leukemic splenocytes using the PJ3 probe (FIG. 5). DNA from spleens of littermate controls showed the IgH gene in its germ-line configuration, whereas DNA from leukemic splenocytes presented extra-rearranged bands, indicating the presence of clonal B cell populations.

The above findings provide an animal model for CLL, the most common human leukemia, and demonstrate that deregulation of the Tcl1 pathway plays a crucial role in CLL pathogenesis. For additional discussion, see Roberta Bichi, Susan A. Shinton, Eric S. Martin, Anatoliy Koval, George A. Calin, Rossano Cesari, Giandomenico Russo, Richard R. Hardy and Carlo M. Croce, Human chronic lymphocytic leukemia modeled in mouse by targeted TCL1 expression, (2002) *Proc. Natl. Acad. Sci.* USA 99 (10): 6955-6960, the disclosure of which is hereby incorporated herein by reference in its entirety.

Example 4

The lymphoproliferative condition exhibited by transgenic animals according to an embodiment of the invention was found to be transplantable to syngeneic animals.

Method to Expand Primary CLL Lymphomas

Moribund Eμ-TCL1 transgenic mice were sacrificed and autopsied. Spleen or, less frequently, lymph node white cells were isolated, counted, diluted in PBS and injected IP in syngeneic mice at 100, 10, 1 million, 100 or 10 thousand cells per mouse. A few cells from affected tissues were stained for IgM, B220, and/or CD5 for FACS analysis. Bone marrow cells were collected for cytogenetics.

TABLE 3

Effects of primary CLL tumors injected in syngeneic mice

91 (founder # 7092) injected Jun. 7, 2002 (10.2 months ago)

| | |
|---|---|
| all males with 100 millions cells died | all females with 100 millions cells died |
| all males with 10 millions cells died | all females with 10 millions cells died |
| all males with 1 millions cells died | all females with 1 millions cells died |
| 4/5 males with 100 thousand cells died | 3/5 females with 100 thousand cells died |
| 3/5 males with 10 thousand cells died | 0/5 females with 10 thousand cells died | tumor features: 1) males may be slightly more affected than females; 2) mortality is cellular dose dependent; 3) homing unknown.

152 (founder # 7092) injected Aug. 28, 2002 (7.5 months ago)

| | |
|---|---|
| all males with 100 millions cells died (surv. = 94) | all females with 100 millions cells are still alive |
| 4/5 males with 10 millions cells died | all females with 10 millions cells are still alive |
| 3/5 males with 1 millions cells died | 4/5 females with 1 millions cells are still alive |
| all males with 100 thousand cells died (surv. = 124) | all females with 100 thousand cells are still alive |
| 3/5 males with 10 thousand cells died | all females with 10 thousand cells are still alive | tumor features: 1) strong sexual dimorphism (only males are affected); 2) mortality is independent of the amount of cells injected; 3) spleen and sometimes liver are the most affected tissues (enlarged lymph nodes were never found).

180 (founder # 7323) injected Oct. 4, 2002 (6.3 months ago)

| | |
|---|---|
| all males with 100 millions cells died (surv. = 94) | all females with 100 millions cells died (surv. = 84) |
| all males with 10 millions cells died (surv. = 107) | 4/5 females with 10 millions cells died |
| all males with 1 millions cells died (surv. = 123) | 3/5 females with 1 millions cells died |
| 4/5 males with 100 thousand cells died | 1/5 females with 100 thousand cells died |
| 4/5 males with 10 thousand cells died | 0/5 females with 10 thousand cells died | tumor features: 1) males are more affected than females; 2) mortality is dependent on the amount of cells injected; 3) neck lymph nodes are the most affected tissues.

178 (founder # 7323) injected Nov. 26, 2002 (4.5 months ago)

| | |
|---|---|
| all males with 10 millions cells died (surv. = 88) | all females with 10 millions cells died (surv. = 78) |
| 1/5 males with 1 millions cells died | 3/5 females with 1 millions cells died | tumor features: 1) females seem to be more affected than males; 2) mortality is dependent on the amount of cells injected; 3) formation of a large amount of ascitic fluid; thymic and mesenteric lymph nodes are the most affected tissues.

TABLE 3-continued

Effects of primary CLL tumors injected in syngeneic mice

232 (founder # 7323) injected Dec. 19, 2002 (3.8 months ago)

| 3/5 males with 10 millions cells died | 0/5 females with 10 millions cells died |
|---|---|
| 1/5 males with 1 millions cells died | 0/5 females with 1 millions cells died | tumor features: 1) males seem to be more affected than females; 2) mortality is dependent on the amount of cells injected; 3) tumor phenotype not yet studied.

243 (founder # 7092) injected Jan. 9, 2003 (3.2 months ago)

all mice are alive + 2 more tumors injected 2 months ago

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A transgenic mouse whose genome comprises a nucleic acid sequence encoding a human TCL1, wherein said sequence is operably linked to a $V_H$ promoter and to a IgH-μ enhancer, wherein said transgenic mouse develops an expanded population of CD5+ B cells compared to a control mouse.

2. The transgenic mouse of claim 1, wherein said $V_H$ promoter comprises a mouse $V_H$ promoter.

3. The transgenic mouse of claim 1, wherein said IgH-μ enhancer comprises a mouse IgH-μ enhancer.

4. The transgenic mouse of claim 1, wherein said mouse develops a lymphocytic leukemia which exhibits characteristics of human B-CLL.

5. A transgenic mouse whose genome comprises a nucleic acid sequence encoding a human TCL1, wherein said sequence is operably linked to a $V_H$ promoter and to a IgH-μ enhancer, and wherein said transgenic mouse develops a lymphocytic leukemia that exhibits characteristics of human B-CLL.

6. The transgenic mouse of claim 5, wherein said $V_H$ promoter comprises a mouse $V_H$ promoter.

7. The transgenic mouse of claim 5, wherein said IgH-μ enhancer comprises a mouse IgH-μ enhancer.

* * * * *

```
                        SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Synthetic construct

<400> SEQUENCE: 1
tgtggtgaca ttagaactga agta                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
caagattagt ctgcaatgct caga                                           24

<210> SEQ ID NO 3
<211> LENGTH: 9
<212> TYPE: DNA
<213> ORGANISM: Mus musculus

<400> SEQUENCE: 3 tgtatgaga                                                             9

<210> SEQ ID NO 4
<211> LENGTH: 7
<212> TYPE: DNA
<213> ORGANISM: Mus musculus

<400> SEQUENCE: 4 tagtagc                                                               7

<210> SEQ ID NO 5
<211> LENGTH: 9
<212> TYPE: DNA
<213> ORGANISM: Mus musculus
```

```
<400> SEQUENCE: 5 tatggtaac                                                              9

<210> SEQ ID NO 6
<211> LENGTH: 12
<212> TYPE: DNA
<213> ORGANISM: Mus musculus

<400> SEQUENCE: 6
tacggtagta gc                                                         12

<210> SEQ ID NO 7
<211> LENGTH: 12
<212> TYPE: DNA
<213> ORGANISM: Mus musculus

<400> SEQUENCE: 7
tatggtaact ac                                                         12

<210> SEQ ID NO 8
<211> LENGTH: 12
<212> TYPE: DNA
<213> ORGANISM: Mus musculus

<400> SEQUENCE: 8
tacggtagta gc                                                         12

<210> SEQ ID NO 9
<211> LENGTH: 12
<212> TYPE: DNA
<213> ORGANISM: Mus musculus

<400> SEQUENCE: 9
tatgatggtt ac                                                         12

<210> SEQ ID NO 10
<211> LENGTH: 9
<212> TYPE: DNA
<213> ORGANISM: Mus musculus

<400> SEQUENCE: 10 tatagtaac                                                              9

<210> SEQ ID NO 11
<211> LENGTH: 12
<212> TYPE: DNA
<213> ORGANISM: Mus musculus

<400> SEQUENCE: 11
tactggtact tc                                                         12

<210> SEQ ID NO 12
<211> LENGTH: 12
<212> TYPE: DNA
<213> ORGANISM: Mus musculus

<400> SEQUENCE: 12
tactgtgcca ga                                                         12

<210> SEQ ID NO 13
<211> LENGTH: 12
<212> TYPE: DNA
<213> ORGANISM: Mus musculus
```

-continued

```
<400> SEQUENCE: 13
gtctattact gt                                                            12

<210> SEQ ID NO 14
<211> LENGTH: 12
<212> TYPE: DNA
<213> ORGANISM: Mus musculus

<400> SEQUENCE: 14
gcaggagaca ga                                                            12

<210> SEQ ID NO 15
<211> LENGTH: 11
<212> TYPE: DNA
<213> ORGANISM: Mus musculus

<400> SEQUENCE: 15
aatggttacg a                                                             11

<210> SEQ ID NO 16
<211> LENGTH: 14
<212> TYPE: DNA
<213> ORGANISM: Mus musculus

<400> SEQUENCE: 16
acggtagtag ccct                                                          14

<210> SEQ ID NO 17
<211> LENGTH: 23
<212> TYPE: DNA
<213> ORGANISM: Mus musculus

<400> SEQUENCE: 17
actccccact acggtagtag cct                                                23

<210> SEQ ID NO 18
<211> LENGTH: 8
<212> TYPE: DNA
<213> ORGANISM: Mus musculus

<400> SEQUENCE: 18 tatggtta                                                                 8

<210> SEQ ID NO 19
<211> LENGTH: 49
<212> TYPE: DNA
<213> ORGANISM: Mus musculus

<400> SEQUENCE: 19
ctatgctatg gactactggg gtcaaggaac ctcagtcacc gtctcctca                    49

<210> SEQ ID NO 20
<211> LENGTH: 49
<212> TYPE: DNA
<213> ORGANISM: Mus musculus

<400> SEQUENCE: 20
ctggtacttc gatgtctggg gcacagggac cacggtcacc gtctcctca                    49
```